United States Patent [19]

Verbicky, Jr. et al.

[11] Patent Number: 4,467,097

[45] Date of Patent: Aug. 21, 1984

[54] METHOD FOR MAKING AROMATIC BIS(ETHERIMIDE)S

[75] Inventors: John W. Verbicky, Jr., Scotia; James A. Cella, Clifton Park; Elbridge A. O'Neil, Jr., Ballston Spa, all of N.Y.

[73] Assignee: General Electric Company, Schenectady, N.Y.

[21] Appl. No.: 426,388

[22] Filed: Sep. 29, 1982

[51] Int. Cl.$^3$ ............................................. C07D 209/48
[52] U.S. Cl. ................................................... 548/461
[58] Field of Search ...................................... 548/461

[56] References Cited
U.S. PATENT DOCUMENTS 3,992,406 11/1976 Markezich ........................ 548/461
4,257,953 3/1981 Williams et al. ................. 548/461
4,273,712 6/1981 Williams ........................... 548/461

Primary Examiner—Donald G. Daus
Assistant Examiner—M. C. Eakin
Attorney, Agent, or Firm—William A. Teoli; James C. Davis, Jr.; James Magee, Jr.

[57] ABSTRACT

A method is provided for making aromatic bis(etherimide)s by effecting reaction between an aromatic bisphenoxide salt and a nitro-substituted N-alkyl phthalimide in the presence of a non-polar organic solvent and an effective amount of a phase transfer catalyst. There is utilized as the phase transfer catalyst, a mixture of a dipolar aprotic solvent and a polyvalent metal salt such as zinc chloride.

10 Claims, No Drawings

METHOD FOR MAKING AROMATIC BIS(ETHERIMIDE)S

CROSS REFERENCE TO RELATED APPLICATIONS

Reference is made to copending application RD-13361 of John W. Verbicky and Brent A. Dellacoletta, filed concurrently herewith and assigned to the same assignee as the present invention, herein incorporated by reference.

BACKGROUND OF THE INVENTION

The present invention relates to a process for making aromatic bis(etherimide)s, based on the reaction between an aromatic bisphenoxide salt and a nitro-substituted phthalimide in the presence of a non-polar organic solvent and a phase transfer catalyst. More particularly, the present invention relates to the use of a mixture of a dipolar aprotic solvent and a zinc salt as a phase transfer catalyst for making aromatic bis(etherimide) using a non-polar organic solvent.

Phase transfer catalysis is a method commonly practiced for conducting reactions in non-polar aprotic solvents when one or more of the reagents required for reaction is/are in the insoluble solid phase and the same is/are in contact with a solution of other reagent(s) of interest.

Typically crown ethers, cryptands and quaternary ammonium or phosphonium salts are used as phase transfer catalysts for the purpose of transferring the insoluble solid reagent(s) into the liquid phase in which the reaction takes place.

Although crown ethers and cryptands are thermally stable, they are quite expensive and in many cases are poor phase transfer catalysts for the desired reaction.

Quaternary ammonium and phosphonium salts, although less expensive than crown ethers and cryptands, are still relatively expensive catalysts which require recycling for cost effective utilization. Further, the quaternary salts tend to be thermally unstable, which leads to catalyst losses via decomposition and contamination of the desired product with by-products from the decomposition process.

The use of dipolar aprotic solvents as the reaction medium for effecting reaction between aromatic bisphenoxide alkali metal salt and N-alkyl nitrophthalimide is also well known, as is the use of cosolvent mixtures, e.g., as much as 80% toluene with 20% dipolar aprotic solvent. The use of such a cosolvent mixture can be moderately effective; however, when 80% or more toluene is used, the yield of product is quite low. For example, using a 90:10 (w/w) ratio of toluene to dimethyl sulfoxide, less than 30% of the desired aromatic bis(ether phthalimide) is obtained after 90 minutes at reflux.

In particular instances, a non-polar solvent, such as toluene can be used with a phase transfer catalyst, such as a tetra-ammonia salt to effect displacement of reactive radicals on a phthalimide nucleus with a mono, or bisalkali metal phenoxide to make aromatic etherimides, as shown by Williams, U.S. Pat. No. 4,273,712, assigned to the same assignee as the present invention. Additional methods for making aromatic bis(etherimide)s using phase transfer catalysts, as shown by Williams et al, U.S. Pat. No. 4,257,953 and Relles et al U.S. Pat. No. 4,247,464. Although valuable results are achieved by using such tetra-ammonia salts as phase transfer catalysts for aromatic bis(etherimide) production, alternative procedures are constantly being sought by those skilled in the art.

The present invention is based on our discovery that aromatic bis(ether phthalimide)s of the formula

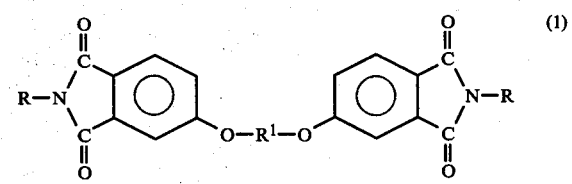

can be made by effecting reaction between an alkali metal bisphenoxide of the formula $$X^1-O-R^1-O-X^2 \qquad (2)$$

and a nitro-substituted N-alkyl phthalimide or N-alkyl phthalimide of the formula

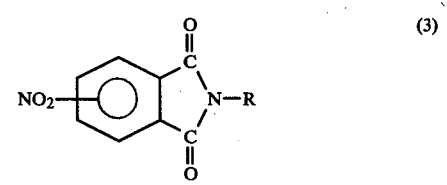

in the presence of a non-polar organic solvent and an effective amount of a phase transfer catalyst in the form of a mixture of a dipolar aprotic solvent and a zinc halide, for example, zinc chloride, where R is a radical selected from hydrogen, a $C_{(1-8)}$ alkyl radical, a $C_{(6-13)}$ aryl radical and mixtures thereof, and $R^1$ is a $C_{(6-30)}$ aromatic organic radical, and $X^1$ and $X^2$ can be the same or different alkali metal ions selected from sodium, potassium, cesium and preferably sodium.

STATEMENT OF THE INVENTION

There is provided by the present invention a method for making aromatic bis(ether phthalimide)s of formula (1) which comprises
 (A) effecting reaction between an alkali bisphenoxide of formula (2) and a nitro-substituted N-alkyl phthalimide of formula (3) in the presence of a non-polar organic solvent, and an effective amount of of a phase transfer catalyst in the form of a mixture of dipolar aprotic solvent and zinc halide, and
 (B) recovering the resulting aromatic bis(ether phthalimide) from the mixture of (A).

Radicals included by R, are for example, phenyl, tolyl, xylyl, naphthyl, chlorophenyl, bromonaphthyl, etc., and alkyl radicals such as methyl, ethyl, propyl, etc. Radicals included by $R^1$ are divalent aromatic radicals, such as phenylene, tolylene, and naphthylene, and $R^1$ more particularly includes

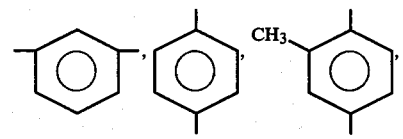

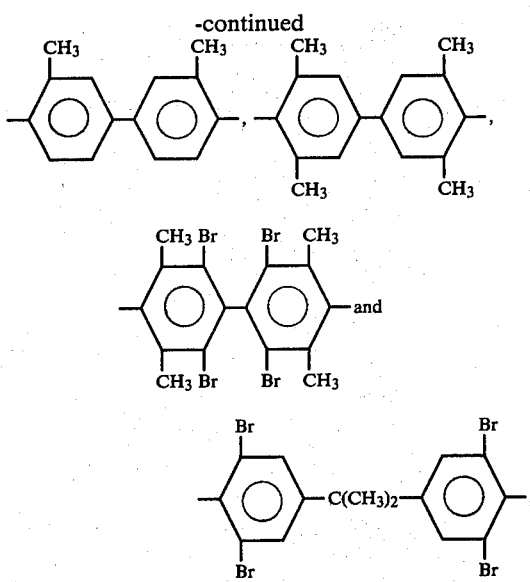

and divalent organic radicals of the general formula,

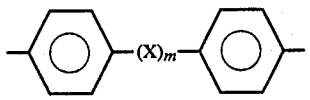

where X is a mamber selected from the class consisting of divalent radicals of the formula,

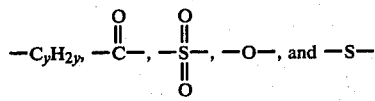

where m is 0 or 1, and y is a whole number from 1 to 5.

The N-alkylphthalimides of formula (3) include, for example, 4-nitro and 3-nitro-N-phenylphthalimide, 4-nitro and 3-nitro-N-methyl-phthalimide, etc.

The solvent used in the present invention is a non-polar organic solvent. So long as this criterion is met, the nature of the non-polar organic solvent is not particularly limited. Representative of such solvents are toluene, benzene, chlorobenzene, xylene, tetrahydrofuran, acetonitrile, octane, etc. Toluene and xylene are preferred considering ease of handling, lack of solvent loss and relative inertness to the reaction of the present invention.

The dipolar aprotic solvent used in the present invention is not limited, and useful dipolar aprotic solvents can be freely selected from those in the art. Exemplary of useful materials are N-cyclohexyl-2-pyrrolidone (NCP), N-N-dimethylacetamide (DMAC), dimethyl sulfoxide (DMSO), dimethyl formamide, N-isopropyl-pyrrolidone, N-methyl-pyrrolidone, bisphenol-A diacetate, etc. NCP is preferred.

The polyvalent metal salt used in combination with the dipolar aprotic solvent of the present invention as a phase transfer catalyst is selected from zinc chloride or zinc bromide.

If desired, mixtures of various alkali metal bisphenoxides of formula (2), nonpolar organic solvents, dipolar aprotic solvents and zinc chloride/zinc bromide may be used.

It is highly preferred to effect reaction under substantially anhydrous conditions per the present invention, although small amounts of moisture can be tolerated. The presence of moisture does, however, lower yield.

The method of the present invention is typically conducted at atmospheric pressure or greater and is most conveniently conducted at atmospheric pressure. The chemistry of the reaction of the method of the present invention is not affected by pressures greater than atmospheric but, due to the greater complexity of the apparatus required for such pressures, nothing is gained by practicing at other than atmospheric pressure. Pressures substantially below atmospheric are not preferred since the boiling point of the solvents present will be lowered, slowing the rate of reaction.

The temperature of reaction is selected so as to be sufficient to reflux the system. At present, we see no substantial benefits to operation at higher temperatures as would be achieved with elevated pressures. For example, refluxing at about 110° C. in toluene provides optimum results. We do not believe that operation at temperatures substantially below 80° C. will prove to be preferred since the reaction rate is too low for most commercial applications. On the other hand, we do not believe that operation at temperatures substantially in excess of about 200° C. will be desired on a commercial scale since side reactions begin to occur with the dipolar aprotic solvent used in the presence of the alkali metal bisphenoxide.

The time of the reaction is in no fashion critical and reaction is merely conducted for a time sufficient to achieve the desired product aromatic bis(ether phthalimide). We contemplate that times on the order of from about 1 hour to about 6 hours will prove to be most generally used for commercially scale operation.

With respect to the ratios of the reactants, solvents and polyvalent metal salts used, these can be relatively free varied and the following discussion is to be taken as representing preferred embodiments of the invention. Unless otherwise indicated, all discussions are with reference to 100 weight parts of the alkali metal bisphenoxide starting material.

The stoichiometry of the reaction of the present invention is such that two mols of N-alkyl phthalimide are required for each one mol of alkali metal bisphenoxide. We generally prefer to react at the stoichiometric level plus or minus 10 mol percent. For example, from about 150 weight parts to about 200 weight parts of N-alkyl phthalimide can be successfully used with 100 weight parts of alkali metal bisphenoxide. As will be appreciated by one skilled in the art, of course, a huge excess of N-alkyl phthalimide could be used and the reaction would proceed with success but separation techniques unnecessary for the mechanism of the reaction would be required, and this would not be preferred.

The nonpolar organic solvent is used in an amount to render the system fluid. As will be appreciated by one skilled in the art, the N-alkyl phthalimide is solid and it is necessary to have sufficient nonpolar organic solvent to dissolve the same. This amount can be very freely varied, and considering the ratios earlier given, usually we prefer to use about 500 weight parts nonpolar organic solvent per 100 weight parts of alkali metal bisphenoxide, most preferably varying no more than plus or minus 20 wt. % therefrom for best results.

The dipolar aprotic solvent is most preferably used in an amount of from about 5 wt. % to about 20 wt. % based on the weight of the alkali metal bisphenoxide.

Below about 5 wt. % a decrease in the rate of reaction and the conversion of the starting materials will begin to be encountered, these effects becoming more prominent as one uses amounts increasingly less than 5 wt. %. At amounts of dipolar aprotic solvent greater than about 20 wt. % no substantial benefits are encountered as compared to the use of about 20 wt. %. We most prefer to use less than 20 wt. % dipolar aprotic solvent.

The zinc metal salt is used in a catalytically effective amount in combination with the dipolar aprotic solvent. Usually we use a minimum of about 0.025 molar equivalents based on alkali metal bisphenoxide and generally do not use more than about 0.1 molar equivalent based on the alkali metal bisphenoxide. Greater amounts of the polyvalent metal salt could be used, of course, but no benefits are achieved thereby.

The final product aromatic bis(ether phthalimide) of the present invention can be converted to aromatic bis(ether phthalic anhydride) following the procedure of U.S. Pat. No. 3,879,428 and the aromatic bis(ether phthalic anhydride) can be converted to a polyamide resin by reaction with an organic diamine following the procedure of U.S. Pat. No. 3,847,867, both hereby incorporated by reference.

The aromatic bis(ether phthalimide) of the present invention is recovered, after reaction, in a conventional fashion, for example as disclosed in U.S. Pat. No. 4,273,712 to Williams, and as disclosed in U.S. Pat. No. 4,257,953, Williams et al, both also hereby incorporated by reference.

The following example is given by way of illustration and not by way of limitation. All parts are by weight and all mixtures are agitated, for example, stirred, during reflux at atmospheric pressure.

EXAMPLE

There was added to a suspension of 1 g of the disodium salt of bisphenol-A in 4.8 grams of toluene, 1.5 g of 4-nitro-N-methylphthalimide, 0.025 molar equivalents of zinc chloride, based on the disodium salt of bisphenol-A and 8.6 weight percent of dipolar aprotic solvent, based on the combined weight of toluene and dipolar aprotic solvent.

The resulting mixture was then heated to reflux at atmospheric pressure for 90 minutes and then sampled for analysis for the resulting 4,4'-bis(N-methylphthalimide-4-oxy)-2,2-diphenylpropane (BPA-BI) whose analysis was based on liquid phase chromatographic analysis using o-terphenyl as an internal standard.

The following results were obtained, where the zinc metal salt and dipolar aprotic solvent, respectively, were omitted in runs 1 and 3, BPA-BI and NCP, DMAC, and DMSO under Dipolar Aprotic Solvent are as previously defined:

| Run | Zinc Metal Salt | Dipolar Aprotic Solvent | BPA-BI Yield (wt. %) |
|---|---|---|---|
| 1 | Not used | NCP | 1.9 |
| 2 | ZnCl$_2$ | DMAC | 40.0 |
| 3 | ZnCl$_2$ | Not used | 0.0 |
| 4 | ZnCl$_2$ | DMSO | 40.0 |
| 5 | ZnCl$_2$ | NCP | 87.1 |

The above results show that the combination of zinc chloride and dipolar aprotic solvent is an effective phase transfer catalyst and NCP and zinc chloride are particularly effective.

The toluene solution of the reaction mixture of Run #5 was then extracted three times with a 0.8% by weight aqueous sodium hydroxide solution at 85° C. The toluene was then removed from the resulting solution by distillation. There was obtained an 85.2% yield of the BPA-BI.

Although the above example is directed to only a few of the very many variables which can be used in the practice of the present invention, it should be understood that the method of the present invention is directed to the use of a much broader variety of alkali metal bisphenoxides, N-alkyl phthalimides, zinc metal salts and dipolar aprotic solvents.

What we claim as new and desire to secure by Letters Patent of the United States is:

1. A method for making aromatic bis(ether phthalimide)s of the formula

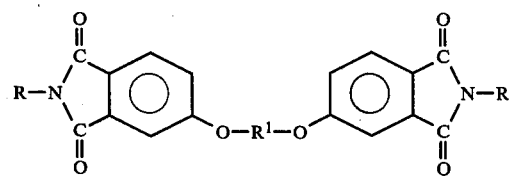

which comprises
(A) effecting reaction between an alkali bisphenoxide of the formula

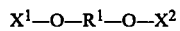

and a nitro-substituted N-alkyl phthalimide of the formula

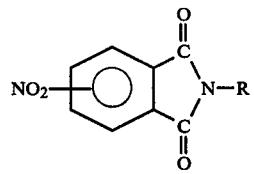

in the presence of a non-polar organic solvent, and an effective amount of a phase transfer catalyst in the form of a mixture of 5 to 20% by weight of dipolar aprotic solvent based on the weight of alkali metal bisphenoxide and 0.025 to 0.1 mole of zinc halide, per mole of alkali metal bisphenoxide and (B) recovering the resulting aromatic bis(ether phthalimide) from the mixture of (A), where R is a group selected from hydrogen, a C$_{(1-8)}$ alkyl group, a C$_{(6-13)}$ aryl group, a halogenated C$_{(6-13)}$ aryl group and mixtures thereof, and R$^1$ is a C$_{(6-30)}$ aromatic organic group selected from the class consisting of

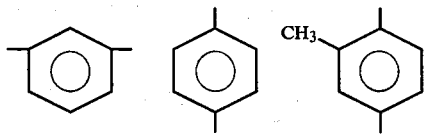

-continued

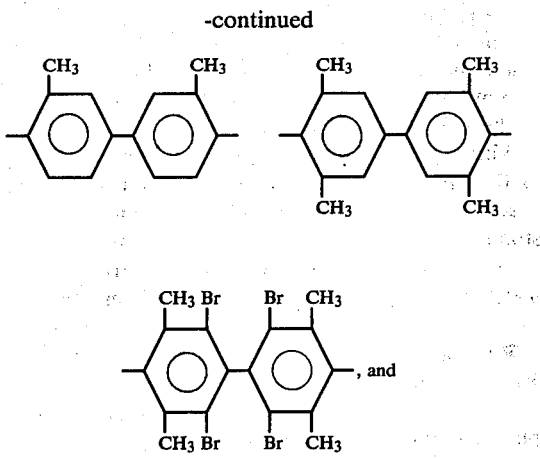

and divalent organic groups of the general formula,

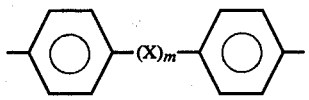

where X is a member selected from the class consisting of divalent groups of the formula,

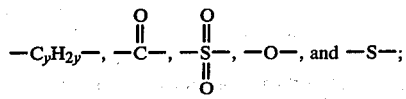

$X^1$ and $X^2$ can be the same or different alkali metal ions selected from the class consisting of sodium, potassium or cesium; m is 0 or 1, and y is a whole number from 1 to 5.

2. The method of claim 1, wherein said zinc halide is zinc chloride.

3. The method of claim 1, wherein said zinc halide is zinc bromide.

4. The method of claim 1 wherein said dipolar aprotic solvent is selected from the group consisting of N-cyclohexyl-2-pyrrolidone, N-N-dimethylacetamide, dimethyl sulfoxide, dimethyl formamide, N-isopropyl-pyrrolidone, N-methyl-pyrrolidone, bisphenol-A diacetate, and mixtures thereof.

5. The method of claim 1, wherein said zinc halide is zinc chloride and said polar aprotic solvent is N-cyclohexyl-2-pyrrolidone.

6. The method of claim 1 conducted under substantially anhydrous conditions.

7. The method of claim 1 wherein said nonpolar organic solvent is selected from the group consisting of toluene, xylene, and mixtures thereof.

8. The method of claim 1 wherein said dipolar aprotic solvent is used in an amount of from about 5 to about 20 wt. % based on the dialkali metal salt of bisphenol-A and said zinc halide used in an amount of from about 0.025 to about 0.1 molar equivalent based on the dialkali metal salt of bisphenol-A.

9. The method of claim 8 wherein about 2 mols plus or minus 10% of said nitro-substituted alkylphthalimide are used per about 1 mol of said dialkali metal salt of bisphenol-A.

10. The method of claim 1 conducted at substantially atmospheric pressure, or above, and at a temperature sufficient to reflux the system.

* * * * *